(12) United States Patent
Pascoguin et al.

(10) Patent No.: US 10,512,425 B2
(45) Date of Patent: Dec. 24, 2019

(54) DERMATOLOGICALLY NON-ABRASIVE BLOOD TESTING USING AN INTERFEROMETRY OPTICAL DESIGN

(71) Applicant: The United States of America as represented by the Secretary of the Navy, San Diego, CA (US)

(72) Inventors: Bienvenido Melvin L. Pascoguin, La Mesa, CA (US); Ryan P. Lu, San Diego, CA (US); Ayax D. Ramirez, Chula Vista, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 507 days.

(21) Appl. No.: 15/228,187

(22) Filed: Aug. 4, 2016

(65) Prior Publication Data
US 2018/0035929 A1 Feb. 8, 2018

(51) Int. Cl.
*A61B 5/145* (2006.01)
*A61B 5/1455* (2006.01)
(Continued)

(52) U.S. Cl.
CPC ........ *A61B 5/14532* (2013.01); *A61B 5/1455* (2013.01); *A61B 5/4839* (2013.01);
(Continued)

(58) Field of Classification Search
CPC . A61B 5/14532; A61B 5/1455; A61B 5/4839; A61B 5/6816; A61B 5/6826;
(Continued)

(56) References Cited

U.S. PATENT DOCUMENTS 4,882,492 A * 11/1989 Schlager ............ A61B 5/14532
250/346
4,901,728 A 2/1990 Hutchison
(Continued)

OTHER PUBLICATIONS

Cote, G.L.; Fox, M.D.; Northrop, R.B., "Noninvasive optical polarimetric glucose . . . " Biomedical Engineering, IEEE; Transactions on, vol. 39, No. 7, Jul. 1992 pp. 752, 756.
(Continued)

*Primary Examiner* — Brandy S Lee
(74) *Attorney, Agent, or Firm* — Naval Information Warfare Center, Pacific; Kyle Eppele; Susanna Torke (57) ABSTRACT

An apparatus, method and system for dermatologically noninvasive testing for blood sugar concentration using an interferometry optical design. The present apparatus, method and system are used to measure the optical properties of blood, without puncturing the skin or drawing blood samples. They incorporate the use of an electromagnetic light source and two optical polarizers. A dermatological sample, e.g., the earlobe, webbing between fingers, is illuminated with polarized electromagnetic light. When the linearly polarized light passes through this dermatological sample, the blood in the dermatological sample acts as an optical rotator due to the optical interaction with the blood sample. The presence of molecular chirality in the blood sample induces optical activity. After the skin is illuminated, a second polarizer finds the orientation of the polarization by maximizing the intensity on the photo detector. As a result, the blood sugar concentration may be determined.

8 Claims, 7 Drawing Sheets

(51) Int. Cl.
*A61B 5/00* (2006.01)
*A61M 5/142* (2006.01)

(52) U.S. Cl.
CPC ....... *A61B 5/7225* (2013.01); *A61M 5/14244* (2013.01); *A61B 5/6816* (2013.01); *A61B 5/6826* (2013.01)

(58) Field of Classification Search
CPC ... A61B 5/7225; A61B 5/6803; A61B 5/7282; A61B 5/742; A61M 5/14244
See application file for complete search history.

(56) References Cited

U.S. PATENT DOCUMENTS

| | | |
|---|---|---|
| 5,070,874 A | 12/1991 | Barnes |
| 5,086,229 A | 2/1992 | Rosenthal |
| 5,222,496 A | 6/1993 | Clarke |
| 5,243,983 A | 9/1993 | Tarr |
| 5,398,681 A | 3/1995 | Kupershmidt |
| 5,519,493 A * | 5/1996 | Reiley .................. G01J 4/04 356/367 |
| 5,533,509 A | 7/1996 | Koashi |
| 6,269,314 B1 | 7/2001 | Iitawaki |
| 2011/0029049 A1* | 2/2011 | Vertikov ............ A61B 5/14532 607/104 |
| 2012/0177576 A1 | 7/2012 | Hu |
| 2014/0235974 A1* | 8/2014 | Higgins ............. A61B 5/14532 600/322 |
| 2016/0015470 A1* | 1/2016 | Border ................ G02B 27/017 600/117 |

OTHER PUBLICATIONS

Jeffrey A. Davis, B. Melvin L. Pascoguin, Ignacio Moreno, and A. Nava-Vega, "Circular-polarization-splitting common-path interferometer . . . " Opt.Lett. 34, 1486-1488 (2009).

\* cited by examiner

DERMATOLOGICALLY NON-ABRASIVE BLOOD TESTING USING AN INTERFEROMETRY OPTICAL DESIGN

STATEMENT OF GOVERNMENT INTEREST

Federally-Sponsored Research and Development

The United States Government has ownership rights in this invention. Licensing inquiries may be directed to Office of Research and Technical Applications, Space and Naval Warfare Systems Center, Pacific, Code 72120, San Diego, Calif., 92152; telephone (619)553-5118; email: ssc_pac_t2@navy.mil. Reference Navy Case No. 102,565.

BACKGROUND OF THE INVENTION

Field of Invention

This disclosure relates to blood testing, and more particularly, non-invasive blood sugar concentration testing.

Description of Related Art

Significant changes in blood sugar concentrations may adversely affect a person's health. For example, spikes in blood sugar can induce blurred vision by causing the lens of the eyeball to swell. At the other end of the spectrum, sugar crashes may cause confusion, difficulty concentrating on daily tasks, light-headedness, irritability and so on. These sudden changes can also affect the decision-making capacity of a person with blood sugar instability. More severe changes in blood sugar concentration—particularly for diabetics—can lead to organ damage, and even death. Therefore, for at least these reasons, it is desirable to monitor changes in blood sugar concentration.

Methods currently exist for monitoring sugar concentration in the blood. These methods include puncturing the skin and taking a blood sample from the fingertips. The blood sample is then analyzed using a device to measure the sugar content of the blood.

Other methods for monitoring blood sugar include methods based on molecular chirality. Optical activities in materials may be induced by the chirality of the molecular building blocks of the material. The presence of molecular chirality in sugar-based solutions is known to induce optical activity as a function of density. See e.g., Jeffrey A. Davis, B. Melvin L. Pascoguin, Ignacio Moreno, and A. Nava-Vega, "Circular-polarization-splitting common-path interferometer based on a zero-twist liquid-crystal display," Opt. Lett. 34, 1486-1488 (2009)(the "Davis Article"). Examples of blood sugar calculations may also be found in the Davis Article. The disclosure for this article is incorporated herein by reference the same as if fully set forth.

One existing way of monitoring blood sugar that incorporates molecular chirality is to take a urine sample, measure its optical activity and derive the blood sugar concentration from the sample. However, urine tests may be inconvenient in that the user may need a private place to collect the sample and the user must wait to urinate in order to collect the sample. There is a need for a method for measuring the sugar content in the blood that does not require a urine sample.

Another existing blood sugar concentration technique that incorporates molecular chirality includes shining a laser beam on a person's eyeball to measure optical activity. This method results in an impairment of vision and thus affects the user's ability to perform an activity that requires vision. There is a need for a way to analyze blood sugar concentration that does not involve impairment of a user's vision.

BRIEF SUMMARY OF INVENTION

The present disclosure addresses the needs noted above by providing an apparatus, system and method for dermatologically noninvasive blood testing.

In accordance with one embodiment of the present disclosure, an apparatus is provided for dermatologically non-invasive blood testing. The apparatus comprises an electromagnetic light source configured to emit electromagnetic light. The apparatus also comprises a linear polarizer device configured to receive the emitted electromagnetic light. The linear polarizer is further configured to linearly polarize the emitted electromagnetic light, and to provide the linearly polarized light in a first polarization state to a blood sample.

The apparatus also includes a polarizer analyzer that is configured to receive the linearly polarized light from the blood sample. The polarizer analyzer is configured to receive the linearly polarized light from the blood sample in a second polarization state. The apparatus also comprises a photodetector that is optically coupled to the polarizer analyzer. The photodetector is configured to detect a change in angle between the first polarization state and the second polarization state.

These, as well as other objects, features and benefits will now become clear from a review of the following detailed description, the illustrative embodiments, and the accompanying drawings.

BRIEF DESCRIPTION OF DRAWINGS

The accompanying drawings, which are incorporated in and form a part of the specification, illustrate example embodiments and, together with the description, serve to explain the principles of the invention. In the drawings.

DETAILED DESCRIPTION OF THE INVENTION

Disclosed herein are an apparatus, method and system for dermatologically noninvasive blood sugar concentration testing. The present apparatus, method and system measure the optical properties of blood to provide blood sugar concentration, without puncturing the skin or drawing blood samples.

The apparatus, method and system incorporate the use of an electromagnetic light source and two optical polarizers. Electromagnetic light is emitted to a first optical polarizer to linearly polarize the light in a first known polarization state. The linearly polarized light is then directed to and through a user's skin, e.g., an earlobe or webbing between the fingers so that the linearly polarized light reaches blood underneath the skin. When the linearly polarized electromagnetic wave passes through this dermatological tissue, the blood in the skin tissue will act as an optical rotator due to the optical interaction with the blood sample. After passing through the skin to the blood, the light is provided to a second optical polarizer in a second polarization state. A photodetector is optically coupled to the second optical polarizer. The photodetector measures optical activity data, which relates to the change in angle between the first polarization state and the second polarization state. Optical activity data are recorded to a data storage medium and provided to a microchip/processor so that the optical activity angle can be determined a. Multiple measurements of this optical activity change may be desired in order to establish a reliable baseline for a user's blood sugar concentration. Edge filtering techniques may be applied to the data in order to aid in detecting sudden changes in blood sugar concentration.

Figure 1:
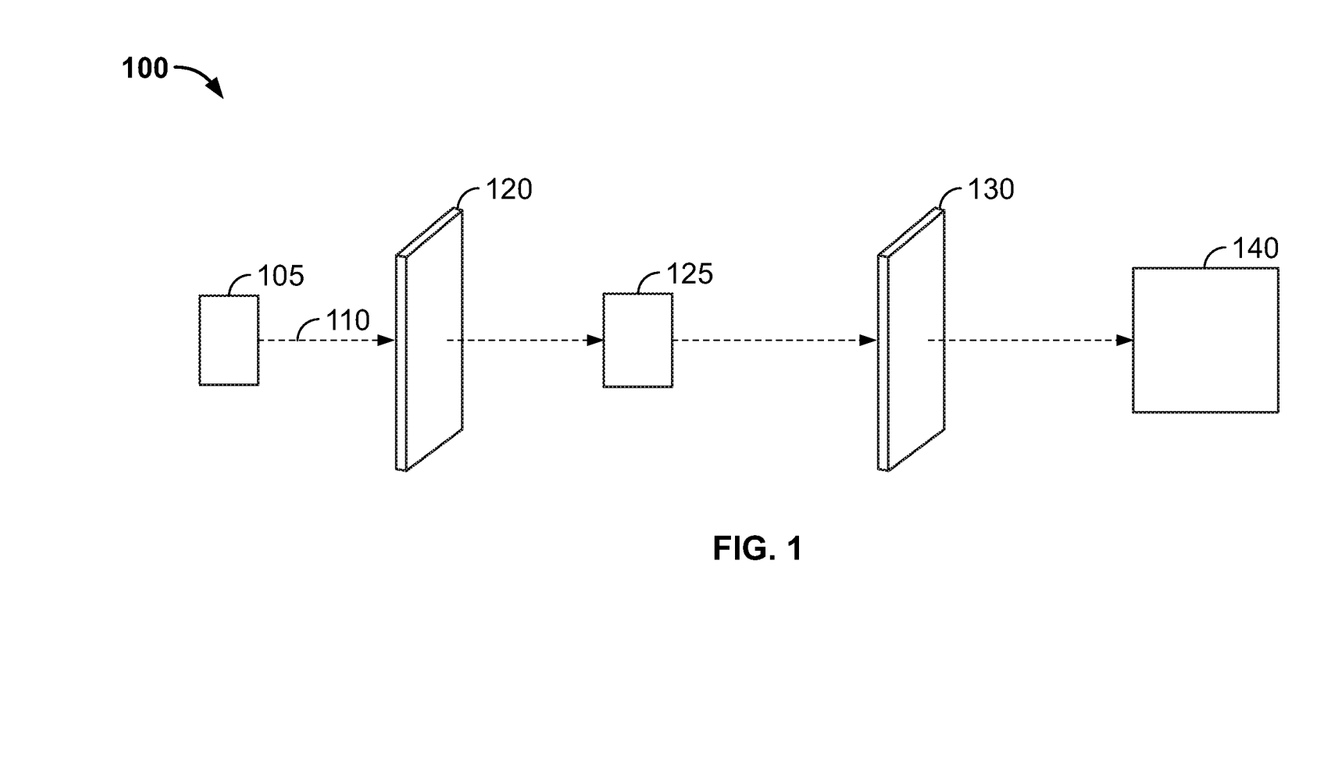
FIG. 1 illustrates optical elements for an apparatus for dermatologically non-invasive blood testing in accordance with one embodiment of the present disclosure.

Referring now to FIG. 1, illustrated are optical elements for an apparatus 100 for dermatologically noninvasive blood testing in accordance with one embodiment of the present disclosure. Light source 105 emits electromagnetic waves via light beam 110 to a linear polarizer 120 in a first polarization state.

The electromagnetic waves emitted from light source 105 via light beam 110 can be microwave, infrared or other types of electromagnetic waves. The light source 105 may be a broadband light source. The light beam 110 may be composed of light that is not in the visible spectrum; for example, the invisible light may be infrared light.

In the example shown in FIG. 1, the polarization orientation of the electromagnetic wave may be zero degrees (0°). Linear polarizer 120 sets a baseline for theta, an initial value for optical activity. The linear polarizer 120 may be purchased as a commercial, off-the-shelf (COTS) item. Linear polarizer 120 is an optical filter that lets light of one polarization, or one direction of propagation, pass. The linear polarizer 120 prevents waves of other polarizations from passing through. In this manner, the direction of the electric field of light beam 110 is well defined, as the electric field of light beam 110 is confined to a single plane along the direction of propagation.

In lieu of having a separate light source 105 and linear polarizer 120, a laser could be used. The laser may emit light that is already linearly polarized. The linearly polarized light may then be provided to a dermatological sample 125 through which blood passes. For purposes of the present disclosure, the dermatological sample 125 therefore provides a blood sample. The dermatological sample 125 may be an earlobe, the webbing area between fingers or toes, or other tissue on various locations of the body. It may be desirable for the dermatological sample 125 to have muscle and yet be relatively fleshy so that a sufficient amount of blood is available for the sample. It may also be desirable for the dermatological sample 125 to be sufficiently thin to permit light to pass therethrough.

The intensity of the light needed from light beam 110 depends upon the body part used for the dermatological sample 125. Generally, for thicker body parts, the light beam 110 must have a higher intensity. For thinner body parts, such as the webbing between fingers or toes, the intensity needed would be lower. Generally, regardless of the body part being used for dermatological sample 125, the light intensity could be significantly lower than that of a standard flashlight. It may be desirable for the device to have a variable intensity such that it could be used for multiple body parts. It may also be desirable to maintain the light source to within a certain intensity range, since some high intensity light, e.g., light above 500 milliwatts (mW), may cause discomfort and burns to the skin. The apparatus 100 may have different settings depending on the thickness or type of a body part. The apparatus 100 may have a control (not shown in FIG. 1), in the form of a dial or otherwise, that is mounted thereon for settings according to different weights or other size measurements of user.

The linearly polarized light passes through the dermatological sample 125 where sugar in the blood causes the linearly polarized light to rotate. The blood in the dermatological sample 125 acts as an optical rotator due to the optical interaction with the dermatological sample 125. Three hundred sixty degrees (360°) is the maximum angle of rotation. The presence of molecular chirality in sugar-based solution induces optical activity as a function of density. When the light exits the sample 125, it is received at a polarizer analyzer 130 in a second polarization state. The polarizer analyzer can be a commercial, off-the-shelf liquid crystal display (LCD) which may operate with or without mechanical movement.

A second angle of polarization (in a second direction) is found after the light passes through the dermatological sample 125. Some of the light may be absorbed by the skin, but the blood will cause optical rotation. A larger change of angle typically corresponds to a higher change in blood concentration. Because the present apparatus 100 is only concerned with a change in sugar concentration, then it is possible for different types of sugars to be measured. For blood sugar concentration, the apparatus 100 may be generally designed to determine changes in blood glucose measurements.

Polarizer analyzer 130 finds the orientation of the polarization by maximizing the intensity on the photodetector 140. This orientation is found according to Malus' law. Under Malus' law, natural light through an ideal polarizer will only allow a P state field through, having an orientation parallel to the transmission axis of the polarizer.

Still in accordance with Malus' law, assume this transmission axis is at an angle θ to the vertical. The beam may then be made to go through another polarizer whose transmission axis is vertical. The amplitude of the electric field transmitted by the first polarizer may be described as $E_{01}$. If so, then only its component, $E_{01} \cos \theta$ parallel to the transmission axis of the second polarizer (polarizer analyzer) will be transmitted.

Further in accordance with Malus' law, the irradiance reaching the detector may then be given by the following equation:

$$I(\theta) = \frac{c\epsilon_0}{2}E_{01}^2\cos^2\theta \quad \text{(Equation 1)}$$

Thus, Malus' Law states as follows:

$$I\theta = I(0)\cos^2(\theta) \quad \text{(Equation 2)}$$

With regard to blood sugar concentration, the blood sugar concentration may be determined according to the following formula:

$$2\Delta\theta = \frac{\Delta n L 2\Pi}{\lambda} \quad \text{(Equation 3)}$$

where $\Delta n$ is the concentration of sugar in the blood, L is the thickness of the medium that the electromagnetic wave is passing through, $\lambda$ is the wavelength of electromagnetic wave, and $\Delta\theta$ is the optical rotation. Any of the data related to Malus' law may be regarded as data related to the change in angle between the first polarization state and the second polarization state. The first polarization state is found at the first linear polarizer 120 before light is transmitted to the dermatological sample 125. The second polarization state is found at the polarizer analyzer 130 after light has passed through the dermatological sample 125 through which blood passes.

The change in θ is important because of optical rotation and molecular chirality. Molecular chirality has essentially the same structure as the reflection of a person's hands. The effect of mirror symmetry in molecular structures induces a shift in the rotation of the linear polarity causing it to rotate. The transmitted electromagnetic wave is still linearly polarized, only rotated by some angle "theta."

The calculation or other determination of the blood sugar concentration may be made with a non-transitory processor-readable data storage medium (not shown in FIG. 1) and/or processor (not shown in FIG. 1) that are operably coupled to the photodetector 140. The data storage medium and processor may be contained in a microchip processor, or microcontroller. Examples of blood sugar calculations may be found in the following paper: Jeffrey A. Davis, B. Melvin L. Pascoguin, Ignacio Moreno, and A. Nava-Vega, "Circular-polarization-splitting common-path interferometer based on a zero-twist liquid-crystal display," Opt. Lett. 34, 1486-1488 (2009). The microchip, processor or microcontroller may be resident on the apparatus 100. Alternatively, it may be operably connected to the apparatus in some manner.

As shown in Equation 1, the greater the concentration of sugar in the blood $\Delta n$, the greater the optical rotation. Also as shown with Equation 1, L is the thickness of the medium that the electromagnetic wave is passing through. It may be desirable to design the apparatus to accommodate body parts with differing thicknesses. In addition, the thickness of one user's body parts may change over time. For example, a user may gain and/or lose weight. If the user is a child, that child may grow. Therefore, it may be desirable to have an adaptable apparatus that adjusts according to body size and/or body dimensions.

The components of the apparatus 100 such as the polarizer analyzer 130 and photodetector 140 may be designed to accommodate various ranges of thicknesses. The thicker the medium, the higher the blood sugar concentration. Thicker media may also require a higher intensity photodetector 140. Photodetector 140 may have a similar intensity level as polarizer analyzer 130. If photodetector 140 has a built-in polarizer, no additional polarizer, e.g., polarizer analyzer 130, is needed. If the photodetector 140 does not have a built-in polarizer, the configuration shown in FIG. 1 is desirable with the polarizer analyzer 130.

As shown in Equation 3, wavelength is a factor in determining the optical activity angle. There are many factors in selecting the wavelength for light beam 110 produced by light source 105. Some wavelengths are more absorptive through liquid than others. Cost may also be a factor. Some photodetectors are more expensive for different wavelengths.

A polarizer analyzer 130 finds the orientation of the polarization by maximizing the intensity on the photodetector 140 as shown in FIG. 1. In this embodiment, it may be desirable that the photodetector 140 not polarize the light as the polarizer analyzer 130 is included for this purpose.

As the polarization is rotated when the light goes through the blood in the dermatological sample, the intensity of the light will vary as a function of the optical angle. The polarizer analyzer 130 and the photodetector 140 will detect the change in the angle.

Photodetector 140 senses the light or other electromagnetic energy passing through the skin to the blood sample. Photodetector 140 measures the intensity of the light and converts the light signals from the dermatological sample 125 into voltage or current. Examples of the types of photodetectors that may be used include photodiodes and photo transistors.

Figure 2:
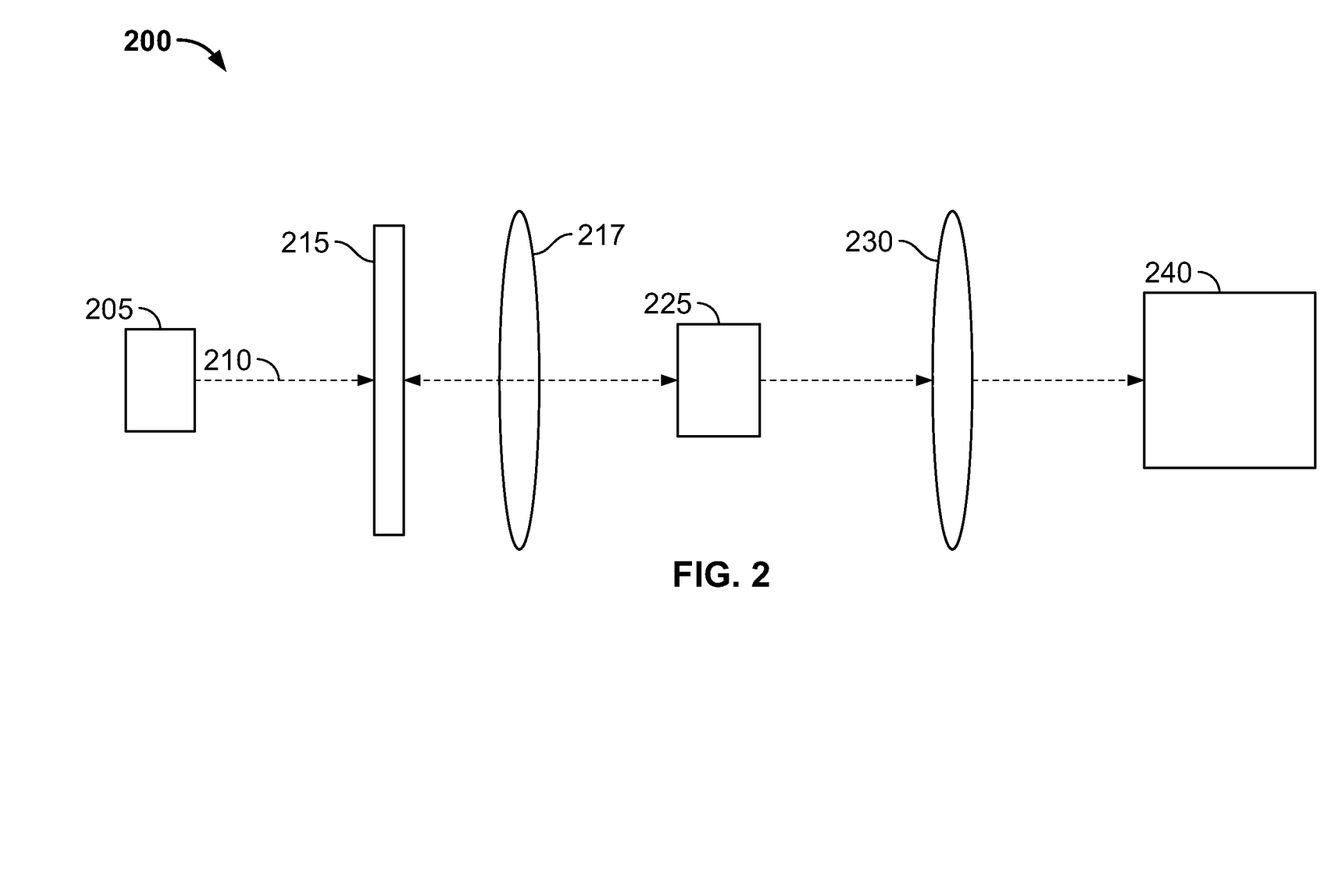
FIG. 2 illustrates optical elements for an apparatus for dermatologically non-invasive blood testing in accordance with another embodiment of the present disclosure.

Improvement of the blood sugar measurement may be obtained by rapidly rotating the polarization of the light source, and using signal processing to accurately measure the optical activity. A quarter-wave plate may aid in this process. Referring now to FIG. 2, illustrated is an apparatus 200 for dermatologically non-invasive blood testing in accordance with another embodiment of the present disclosure. In FIG. 2, the apparatus 200 includes an electromagnetic light source 205, a quarter wave plate 215, a linear polarizer 217 (that provides light to a dermatological sample 225), a polarizer analyzer 230 and a photodetector 240.

In FIG. 2, electromagnetic light source 205 emits light beam 210 to quarter wave plate 215. The quarter wave plate 215 optically rotates the polarity of the received light from laser 205. An alternative and more complicated process would be rotating the light source 205 to change the direction of light beam 210. In the present illustration, the light is emitted from light source 210 at forty-five (45) degrees (°). After the light beam 210 is received at the quarter wave plate 215, the emitted light is received by the linear polarizer 217.

The linear polarizer 217 linearly polarizes the received light in one direction. After the light beam 210 passes through the blood in the dermatological sample 225, the light beam 225 is received at a polarizer analyzer 230 in a second polarization state. Optical rotation occurs after the light passes through the dermatological sample 225 so that the light is propagated in a different direction than before the light hit the dermatological sample. The polarizer analyzer 230 is rotated to maximize the signal. The angle that gives the maximum intensity is the second polarization state.

The linearly polarized light from the polarizer analyzer 230 is received at photodetector 240. In this embodiment, the photodetector 240 is unpolarized. However, if photodetector 240 were polarized, the polarizer analyzer 230 may not be needed.

Polarizer analyzer 230 and photodetector 240 are used to measure polarization, which is a function of electromagnetic oscillation. When the polarization is rotated, the intensity will vary as a function of the angle. The highest intensity will be the state of polarization, and the optical angle can be detected in accordance with Malus' law.

Once the polarization is known, the change of polarization can be computed with computer instructions and a processor configured to execute the instructions. The computation should be performed according to the type of sugar being detected.

Linear polarizer 217 and polarizer analyzer 230 can be rotated and synchronized to find the average optical activity angle. This measurement may be taken multiple times in order to find the average angle. However, it may be desirable, on the other hand, to limit the number of times the measurement is taken in order reduce power consumption from the power source (not shown), e.g., a small battery. Power source should be operably coupled to components needing power, e.g., the light source 210, photodetector 240 and processor (not shown in FIG. 2).

In lieu of light source 210, sunlight may be used as a broadband electromagnetic wave source. Because sunlight contains various ranges of electromagnetic (infrared and ultraviolet) radiation, filters may be used to select narrow wavelengths of electromagnetic wave. The filters may be color filters. Green filters may be suitable for the system because sunlight emits more green. If a red filter is used to filter out light at, for example, around 639 nanometers (nm), red light would be present with a narrow band. A narrow band means a narrow frequency, maybe 638-640 nm. Using a broad-band light source or a light bulb, the filter aids in providing a narrow source. Electromagnetic light source 210 may be a broadband light source, which may be useful because most detectors are frequency sensitive. The user may want to stay within that range of detector. For example, if a user were to go outside the range of a red-sensitive detector with blue light, the blue light may distort the signal.

The optical activity data that is measured and acquired can be stored in a computer chip, such as a microcontroller. Optical activity data measured using the apparatus 200 is data related to the angles of polarization for the apparatus 200, particularly linear polarizer 217 in a first polarization state and polarizer analyzer 230 in a second polarization state.

Figure 3A:
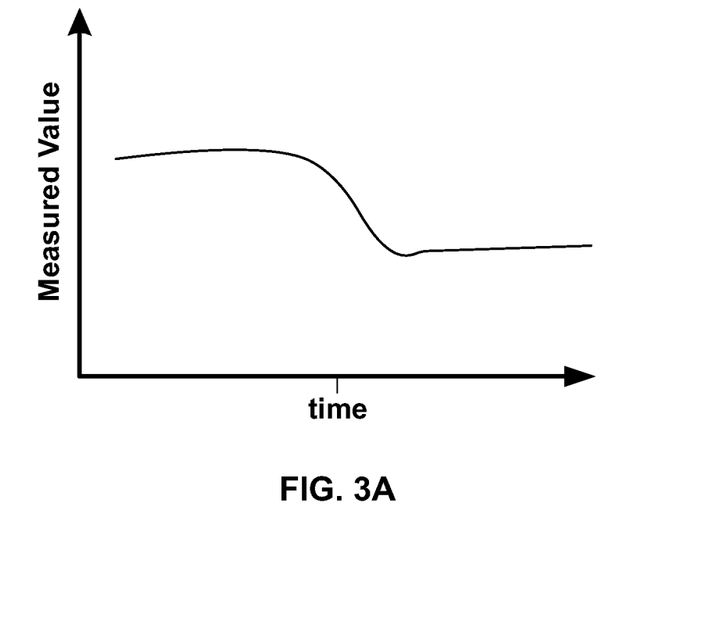
FIG. 3A shows an example of initial measured values of the optical activity angle in accordance with one embodiment of the present disclosure.

It may be desirable to take an initial measurement of blood sugar over time in order to obtain a baseline. Referring now to FIG. 3A, shown is a graphical representation of a measured value of blood sugar over time.

The graphical illustration of FIG. 3A is produced by a feedback algorithm, and shows a collection of measured values, which can be, e.g., angle or density of sugar. The feedback keeps measuring an angle, saves it and repeats that process until sufficient data is taken. The feedback algorithm can take as many points of data as necessary, limited by aspects such as battery power.

The importance of the present technique is how blood sugar changes over time. The present technique is not dependent upon a direct measurement where a blood meter measures the exact amount of density. It's a relative measurement.

After this initial value is taken, digital signal processing (DSP) or other standard edge enhancement filtering technique may be used on the optical activity data. The digital signal processing may be built into a blood testing apparatus, a chip, microcontroller or other device, any of which could have an interface with a smart phone. The interface may occur through a Bluetooth chip which would reduce the load on a battery for the blood sugar testing apparatus of the present disclosure, as the battery would not have to expend energy on a computation.

Figure 3B:
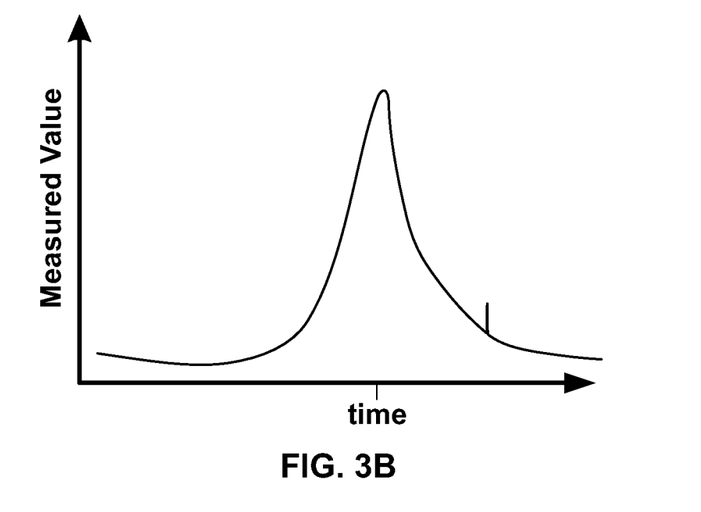
FIG. 3B shows edge filtered data in digital signal processing (DSP) in accordance with one embodiment of the present disclosure.

Using the DSP, a sudden spike in the blood sugar can be detected and warn the user to reconsider his/her decision. Referring now to FIG. 3B, illustrated is an example of data on which edge enhancement filtering has been applied. As seen, a sudden spike in blood sugar is illustrated by the edge enhanced data. Other DSP techniques include a derivative filter, Helburg filter, and numerous other filters known in the art. The filtering may aid in exaggerating the received optical data to better illustrate significant changes.

The blood sugar testing apparatus may be incorporated into a larger system, including a system that permits it to connect to another device in order to automatically inject insulin at the appropriate times.

Figure 4:
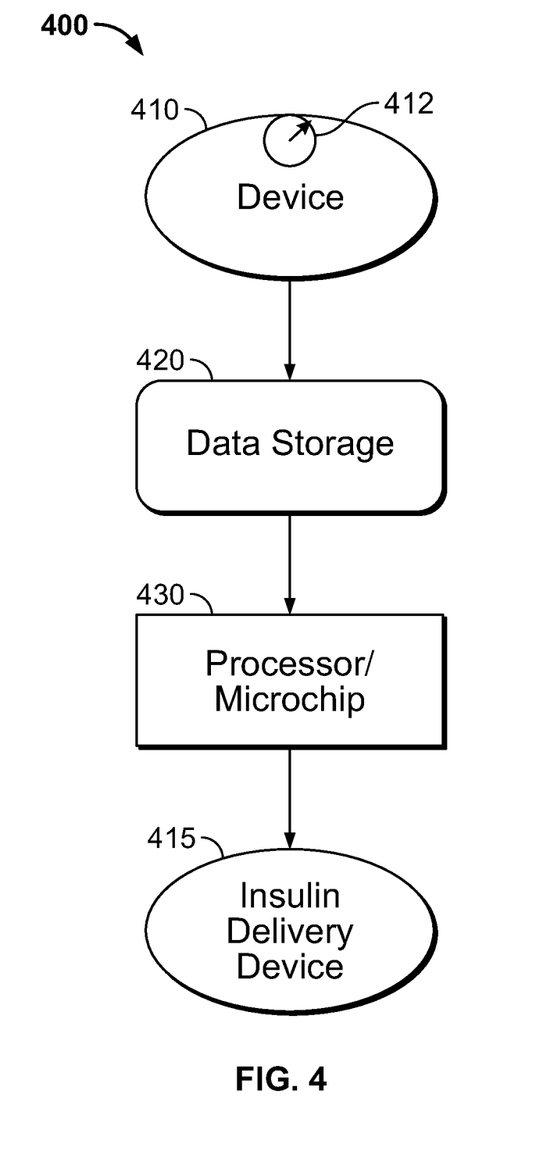
FIG. 4 illustrates a system for dermatologically noninvasive blood testing in accordance with one embodiment of the present disclosure.

Referring now to FIG. 4, illustrated is a system for dermatologically noninvasive blood sugar testing. The system may include an apparatus 410 for dermatologically noninvasive blood testing using an interferometry design. Using interferometry techniques, electromagnetic waves may be superimposed onto each other in order to extract information about the waves. The present system, method and apparatus incorporate interferometry in order to compare polarization states.

The apparatus 410 that is a part of the system of FIG. 4 may be the same or similar to that described in FIG. 1. When the user receives information that his/her blood sugar concentration is varying too broadly, then the user may manually inject himself/herself with insulin. Alternatively, the insulin may be automatically delivered via system 400.

As shown in FIG. 4, the apparatus 410 has a control 412 in order to permit the user to manually adjust for various body sizes and weights. Apparatus 410 can be synced with existing technology such as an insulin delivery device 415 to automate insulin or glucose body intake by constantly maintaining a safe blood sugar level. The apparatus 410 for dermatologically noninvasive blood testing provides the functions to receive optical activity data and determine a change in optical angle. Optical activity data includes the following: (a) the direction in which the linearly polarized light propagated prior to reaching the dermatological sample; and (b) the direction in which the light propagated after leaving the dermatological sample.

Data storage medium 420 may be operably coupled to the apparatus 410 so that data storage medium 420 receives optical activity data from the apparatus 410. Data storage medium 420 can take on a number of forms, including flash storage. The data may be received at the data storage medium 420 at a rate expressed in samples per second. The data may be received by data storage medium 420 from apparatus 410 at a number of different rates suitable to obtain the needed optical activity data. A processor 430 may be operably coupled, electrically or otherwise, to the data storage medium 420. The processor 430 may be small, such as a microchip. The processor 430 may analyze the data and perform calculations related to the data. The processor 430 may be operably coupled to an insulin delivery device 415.

Battery, disposed in apparatus 410, may be operably coupled to the light source inside apparatus 410. The battery in apparatus 410 may also be operably coupled to processor 430. Insulin delivery device 440 may have its own power source, or it may be operably coupled to the battery of apparatus 410. In lieu of the battery disposed within apparatus 410, another power source such as an outlet may be used.

The system 400 that comprises the apparatus 410, data storage device 420, processor 430 and insulin delivery device 415 may be attached to a user's body or worn by a user. In this manner, the system 400 may determine when a user's blood sugar concentration has gone outside an acceptable range. The system 400 may then determine, via the insulin delivery device 440, that one or more doses of insulin are needed. The system 400 may be configured to automatically deliver the appropriate amount of insulin to the user. Software resident in the apparatus 410 or insulin delivery system 415 may determine that such insulin is needed. Power may be supplied to the insulin delivery device 415 via a power source that is contained within the insulin delivery device 415. Alternatively, insulin delivery device 415 may operate from power supplied by battery or other power source.

As noted hereinabove, the apparatus 410 may be attached to different parts of the body. Because the size of these body parts may vary from person to person, the apparatus 410 may require a calibration from another blood sugar meter, such as one contained in insulin delivery device 415, to obtain an initial value. If the thickness of the blood volume on a limb could be measured, then there may be no need for calibration due to the physics of optical activity in sugar solution, if we know the thickness of the solution.

Figure 5:
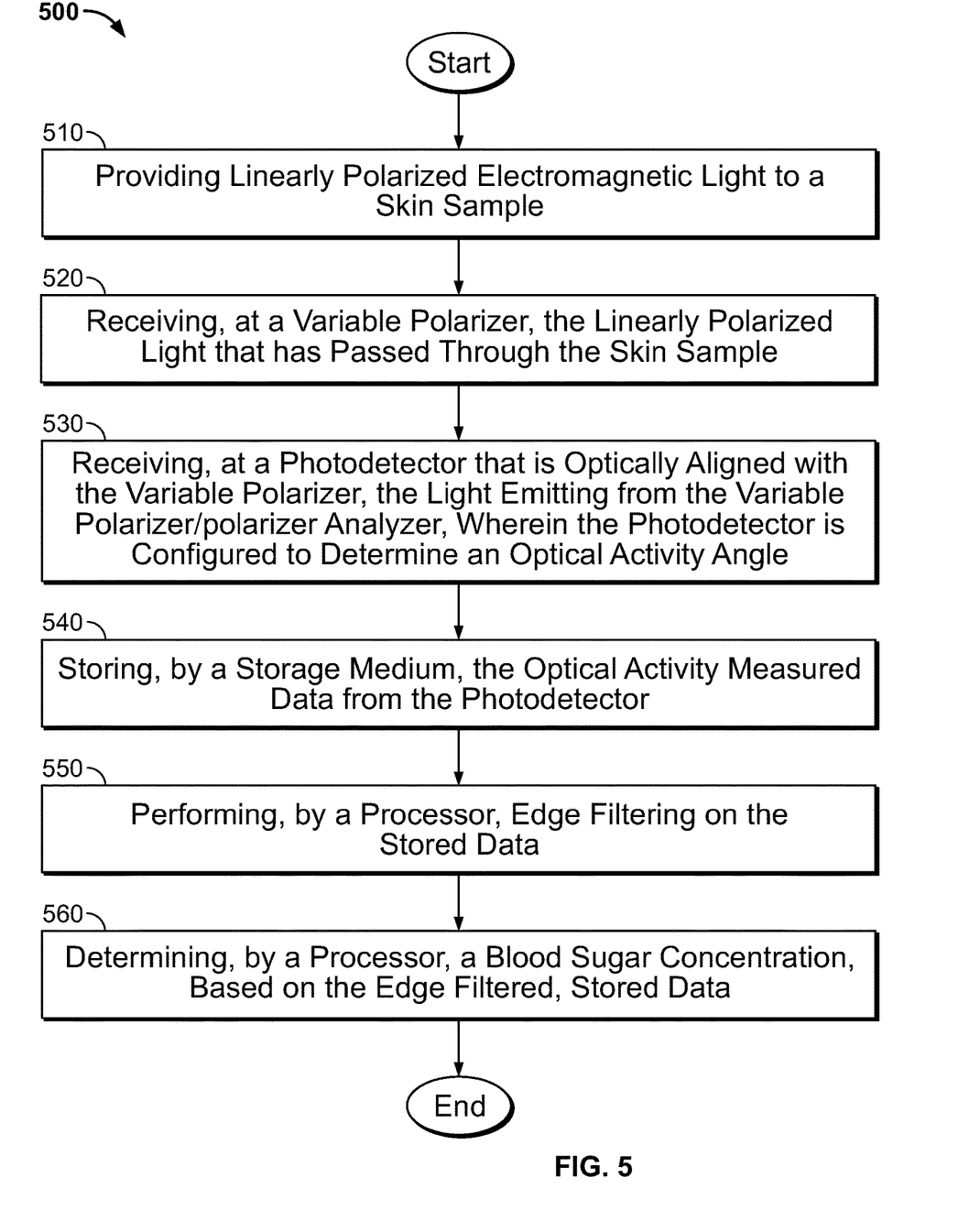
FIG. 5 illustrates a flow diagram for a method for dermatologically noninvasive blood testing in accordance with one embodiment of the present disclosure.

Referring now to FIG. 5, illustrated is a method 500 for dermatologically noninvasive blood sugar concentration testing in accordance with one embodiment of the present disclosure. At step 510, the method includes providing linearly polarized electromagnetic light to a skin sample. A laser may be used, or an electromagnetic light source may be combined with a linear polarizer. This linearly polarized electromagnetic light is provided in a first polarization state. At step 520, the method includes receiving, at a polarizer analyzer, the linearly polarized light that has passed through the skin sample. Light is received at the polarizer analyzer in a second polarization state. At step 530, the method further includes receiving, at a photodetector that is optically aligned with the polarizer analyzer, the light emitted from the polarizer analyzer. The photodetector is configured to measure an optical activity angle so that a blood sugar concentration is determined. At step 540, the method includes storing, by a non-transitory processor-readable storage medium, the optical activity data from the photodetector. At step 550, the method includes performing, by a processor, edge filtering on the stored data. At step 560, the method includes determining, by a processor, a blood sugar concentration, based on the edge filtered, stored data.

Figure 6A:
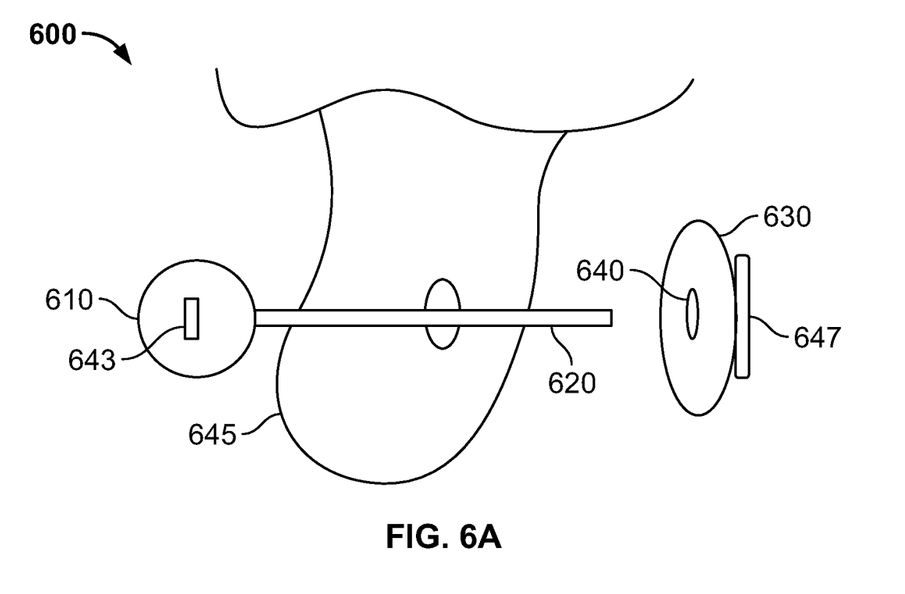
FIG. 6A illustrates the apparatus for noninvasive blood testing as an earring as worn on an earlobe, in accordance with another embodiment of the present disclosure.

There are numerous ways to attach this device to a person's body such as the earlobe, nose, in-between fingers, or in-between toes. Referring now to FIG. 6A, illustrated is an example of an apparatus for dermatologically noninvasive blood sugar concentration testing. In FIG. 6A, the apparatus 600 is designed to be attached to a user's earlobe and fashioned as an earring. The apparatus 600 includes an anterior portion 610 designed to be disposed at the front of a user's earlobe. The anterior portion 610 is fixedly attached to a post 620. The anterior portion 630 is the earring back in this embodiment. The anterior portions is designed to be positioned on the post 620 via aperture 640. The inner diameter of aperture 640 may be only slightly larger than the outer circumference of post 620 so that a snug fit may be obtained. The device 600 may also include a storage medium in one of portions 610, 630. When a reading of blood sugar concentration is desired, the device 600 may be hooked up to a computer (not shown) which may include a processor. The storage medium may communicate blood sugar concentration data to the processor. The attached computer may then perform edge filtering and other calculations pertaining to blood sugar concentration. The device 600 may attach to a user's ear and/or nose and can be fashioned as a nose ring. In lieu of the post 620, the device 600 may include a screw so that it can be screwed on to a user's ear or nose if the user does not have a piercing suitable for post 620 to go through. A small battery 647 may be disposed at the rear of back 630 to power the device 600. In lieu of and/or in addition to battery 647, an energy harvesting device 643 such as a small solar cell may be used to aid in powering the device. In the present illustration, the energy harvesting device 643 is attached to the anterior portion 610 so that it may receive sunlight when worn outside by the user.

Figure 6B:
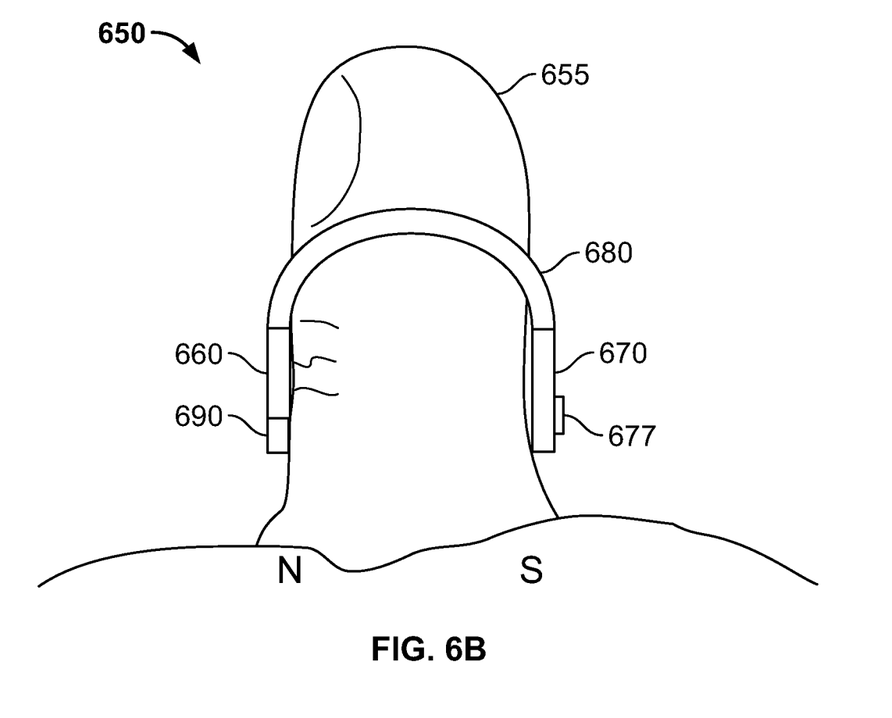
FIG. 6B illustrates the apparatus for noninvasive blood testing as a clamped device that can be used on different body parts, such as a finger, in accordance with another embodiment of the present disclosure.

Alternatively, the device can be fashioned as a two-part magnetic device that can be attached to other body parts. Referring now to FIG. 6B, illustrated is another embodiment of an apparatus for dermatologically noninvasive blood sugar concentration testing. In FIG. 6B, the apparatus 650 is placed on a user's thumb 655 in order to determine a user's blood sugar concentration. The device includes an anterior portion 660 and a posterior portion 670 that may be adjoined by a clamp 680. In lieu of a clamp 680, a magnet may be provided so that the first portion 660 is held close to the second portion 670 via magnetic attraction. As shown at the bottom of FIG. 6B, the magnet can have a north and south pole for attraction between the anterior portion 660 and posterior portion 670.

Included within the first portion 660 of the device are the elements necessary to provide linearly polarized light to the user's thumb or other body part. For example, an electromagnetic light source and a linear polarizer may be contained in the anterior portion 660. Included within the posterior portion 670 may be a polarizer analyzer and a photodetector. Other elements such as a microchip may be included for edge filtering. The microchip may also be used to implement or execute calculations related to blood sugar concentration. As used herein, the anterior portion 660 means the portion where the light is emitted into the user's thumb 655, such as with a light source and a linear polarizer. As used herein, the posterior portion 670 refers to the portion that receive light emitted from the blood sample in the user's thumb 655, such as with a variable polarizer and photodetector. A battery 677 may be provided in order to power the device.

The device may also be fashioned as other articles designed to be worn by the user. For example, the device may be designed for attachment in-between the fingers or toes at the webbing in the fingers or toes. In another embodiment, the device could be fashioned as a pair of gloves or socks.

Figure 6C:
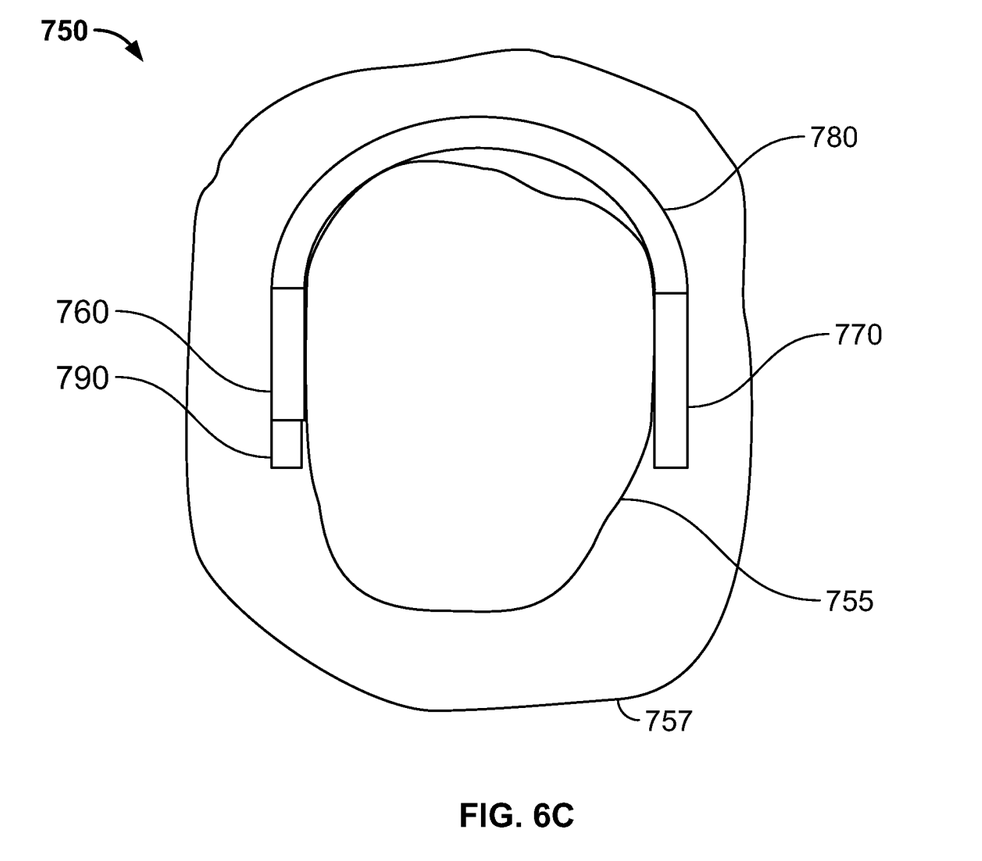
FIG. 6C illustrates another embodiment of an apparatus for dermatologically noninvasive blood sugar concentration testing, in accordance with another embodiment of the present disclosure.

Interfacing with flexible electronics can allow seamless integration with clothing. In this manner, the device can be worn as an article of clothing, such as a shirt, underwear or as part of a pair of pants. Referring now to FIG. 6C, illustrated is a top cross-sectional view of another embodiment of an apparatus for dermatologically noninvasive blood sugar concentration testing. In FIG. 6B, the apparatus 750 is placed around a user's thigh 755 inside a user's clothing, e.g., inside the diameter of a pants leg 757 in order to determine a user's blood sugar concentration. The device 750 includes a first portion 760 and a second portion 770 that may be adjoined by a clamp 780. In lieu of a clamp 780, a magnet may be provided so that the first portion 760 is held close to the second portion 770 via magnetic attraction.

Included within the first portion 760 of the device are the elements necessary to provide linearly polarized light to the user's thigh or other body part. For example, an electromagnetic light source and a linear polarizer may be contained in the anterior portion 760. Included within the posterior portion 770 may be a polarizer analyzer and a photodetector. Other elements such as a microchip may be included for edge filtering, and calculations related to blood sugar concentration. As used herein, the anterior portion 760 means the portion where the light is emitted into the user's thumb 755, such as with a light source and a linear polarizer. As used herein, the posterior portion 770 refers to the portion that receive light emitted from the blood sample in the user's leg 755, such as with a variable polarizer and photodetector.

In lieu of a pant leg 757, the device could be adapted to be worn inside the sleeve of a shirt, inside a shoe, on the side of the abdomen or any number of other locations on the body.

With the improvement of energy harvesting, this device can be powered by the user's motion. Any wavelength of light can be used. One way to power the device is to use the sunlight both for solar power and as a broadband light source. Because sunlight can have a broad range of wavelengths in just the infrared range. Filters may be used to select narrow bands of wavelengths, if desired. Lenses may be used to aid in focusing and collimating the light.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. An apparatus for dermatologically noninvasive blood sugar testing, the apparatus comprising:
    an electromagnetic light source configured to emit electromagnetic light;
    a linear polarizer device configured to receive the emitted electromagnetic light, the linear polarizer device being further configured to linearly polarize the emitted electromagnetic light, and to provide the linearly polarized light in a first polarization state to a blood sample;
    a polarizer analyzer that is configured to receive the linearly polarized light in a second polarization state from the blood sample, wherein the polarizer analyzer is a liquid crystal display having an interferometry design configured to detect optical activity; and
    a photodetector optically coupled to the polarizer analyzer, the photodetector being configured to detect a change in angle between the first polarization state and the second polarization state,
    wherein the apparatus is configured to be attached to a user's body or clothing such that the apparatus is portable as it detects the change in angle between the first polarization state and the second polarization state,
    a non-transitory processor-readable data storage medium communicably coupled to the photodetector, the data storage medium being configured to receive and record data related to the change in angle between the first polarization state and the second polarization state.

2. The apparatus of claim 1, wherein the non-transitory processor-readable data storage medium stores processor-executable instructions, the apparatus further comprising:
    a processor communicably coupled to the data storage medium; and
    wherein the processor-executable instructions, when executed, cause the processor to perform edge filtering on the recorded data related to the change in angle between the first polarization state and the second polarization state.

3. The apparatus of claim 2, further comprising:
    processor-executable instructions which, when executed, cause the processor to determine a blood sugar concentration change based on the change in angle between the first polarization state and the second polarization state.

4. The apparatus of claim 3, wherein the apparatus is adapted to be coupled to an insulin delivery device, wherein the insulin delivery device is configured to receive the determined blood sugar concentration change, and wherein the insulin delivery device is adapted to deliver insulin to a user, without user intervention, and wherein the insulin delivery device is configured to determine when an insulin level of the user is outside of an acceptable range.

5. The apparatus of claim 4, wherein the insulin delivery device is further configured to deliver insulin to the user in an amount that brings the insulin level of the user within the acceptable range.

6. A method for dermatologically noninvasive blood sugar testing, the method comprising:
    providing, by at least one light source, linearly polarized electromagnetic light in a first polarization state, wherein the linearly polarized light is configured to be provided to a blood sample,
    receiving, at a polarizer analyzer, linearly polarized light in a second polarization state from the blood sample, wherein the polarizer analyzer is a liquid crystal display having an interferometry design configured to detect optical activity;
    detecting, at a photodetector, a change in angle between the first polarization state and the second polarization state,
    wherein the at least one light source, the polarizer analyzer, and the photodetector are configured to be attached to a user's body or clothing such that the at least one light source, the polarizer analyzer, and the photodetector are portable as the photodetector detects the change in angle between the first polarization state and the second polarization state,
    receiving and recording, at a non-transitory processor-readable data storage medium communicably coupled to the photodetector, data related to the angle between the first polarization state and the second polarization state.

7. The method of claim 6, further comprising:
    causing, by processor-executable instructions executed on a processor, the processor to determine a blood sugar concentration change based on the data related to the angle between the first polarization state and the second polarization state.

8. A method for dermatologically noninvasive blood sugar testing, the method comprising:
    providing, by at least one light source, linearly polarized electromagnetic light in a first polarization state, wherein the linearly polarized light is configured to be provided to a blood sample, receiving, at a polarizer analyzer, linearly polarized light in a second polarization state from the blood sample, wherein the polarizer analyzer is a liquid crystal display having an interferometry design configured to detect optical activity;

detecting, at a photodetector, a change in angle between the first polarization state and the second polarization state, wherein the at least one light source, the polarizer analyzer, and the photodetector are configured to be attached to a user's body or clothing such that the at least one light source, the polarizer analyzer, and the photodetector are portable as the photodetector detects the change in angle between the first polarization state and the second polarization state, performing, at a processor, edge filtering on data related to the change in angle between the first polarization state and the second polarization state.

* * * * *